United States Patent [19]

Nuesslein et al.

[11] 4,369,185
[45] Jan. 18, 1983

[54] FUNGICIDAL 2-SULFINYL-5-SULFONYL-1,3,4-THIADIAZOLE DERIVATIVES

[75] Inventors: Ludwig Nuesslein; Dietrich Baumert; Georg-Alexander Hoyer; Ernst A. Pieroh, all of Berlin, Fed. Rep. of Germany

[73] Assignee: Schering Aktiengesellschaft, Berlin and Bergkamen, Fed. Rep. of Germany

[21] Appl. No.: 178,703

[22] Filed: Aug. 12, 1980

[30] Foreign Application Priority Data

Aug. 13, 1979 [DE] Fed. Rep. of Germany ...... 2933008

[51] Int. Cl.³ .................... A01N 43/82; C07D 285/12
[52] U.S. Cl. .................................. 424/270; 548/136; 548/142
[58] Field of Search .................. 424/270; 548/142

[56] References Cited

U.S. PATENT DOCUMENTS 3,753,999  8/1973  Tempel et al. ................. 548/142
4,097,669  6/1978  Reisdorff et al. .............. 548/142

FOREIGN PATENT DOCUMENTS 1568552  5/1969  France ........................... 548/142

OTHER PUBLICATIONS

Sassiver et al., J. Med. Chem., vol. 9, pp. 541-545 (1966).

*Primary Examiner*—Alton D. Rollins
*Attorney, Agent, or Firm*—Michael J. Striker

[57] ABSTRACT

A method for production of novel antifungal 1,3,4-thiadiazole derivatives having a composition of the general formula

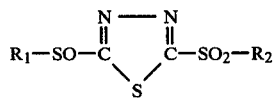

wherein $R_1$ and $R_2$ are independently alkyl with from 1 to 6 carbon atoms, alkenyl with from 2 to 6 carbon atoms, alkinyl with from 2 to 6 carbon atoms or cycloalkyl with from 3 to 6 carbon atoms is provided. 1,3,4-thiadiazole derivatives of a composition of the general formula

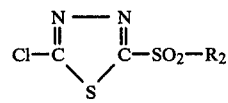

are reacted with a compound having the composition of the general formula $R_1$-SH resulting in compounds of a composition having the formula

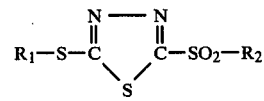

which in turn are oxidized with an organic or inorganic oxidant.

6 Claims, No Drawings

FUNGICIDAL 2-SULFINYL-5-SULFONYL-1,3,4-THIADIAZOLE DERIVATIVES

BACKGROUND OF THE INVENTION

1. Field of the Invention

The present invention relates to new fungicidal 2-sulfinyl-5-sulfonyl-1,3,4-thiadiazole derivatives, a method of production of these compounds as well as a method of controlling fungi.

2. Brief Description of the Background of the Invention Including Prior Art

It is known to produce certain fungicidal 2,5-sulfonyl-1,3,4-thiadiazole derivatives (German Patent DE-PS No. 16 95 847). However, these do not always show a satisfactory action, in particular against grain fungi.

SUMMARY OF THE INVENTION

1. Purposes of the Invention

It is an object of the present invention to provide a fungicidal material particularly active against grain fungi.

It is another object of the present invention to provide a method for the production of certain 1,3,4-thiadiazole derivatives.

It is a further object of the present invention to provide a method for controlling fungi.

These and other objects and advantages of the present invention will become evident from the description which follows.

2. Brief Description of the Invention

The present invention provides a 2-sulfinyl-5-sulfonyl-1,3,4-thiadiazole derivative of a composition having the general formula

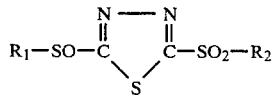

wherein $R_1$ and $R_2$ are independently alkyl with from 1 to 6 carbon atoms, alkenyl with from 2 to 6 carbon atoms, alkinyl with from 2 to 6 carbon atoms or cycloalkyl with from 3 to 6 carbon atoms. Preferred 2-sulfinyl-5-sulfonyl-1,3,4-thiadiazole derivatives include those wherein $R_1$ and/or $R_2$ are methyl, ethyl, propyl, isopropyl, cyclopropyl, 2-propenyl, 2-propinyl, n-butyl, isobutyl, sec.-butyl, n-pentyl, sec.-pentyl, isopentyl, sec.-hexyl or isohexyl. Preferably the above 2-sulfinyl-5-sulfonyl-1,3,4-thiadiazoles have admixed a carrier and/or auxiliary materials suitable in a fungicide mixture.

Preferred 2-sulfinyl-5-sulfonyl-1,3,4-thiadiazole derivatives include:
2-ethylsulfinyl-5-butylsulfonyl-1,3,4-thiadiazole,
2-isopropylsulfinyl-5-isopropylsulfonyl-1,3,4-thiadiazole,
2-ethylsulfinyl-5-methylsulfonyl-1,3,4-thiadiazole,
2-ethylsulfinyl-5-ethylsulfonyl-1,3,4-thiadiazole,
2-ethylsulfinyl-5-propylsulfonyl-1,3,4-thiadiazole,
2-ethylsulfinyl-5-isopropylsulfonyl-1,3,4-thiadiazole,
2-ethylsulfinyl-5-sec.-butylsulfonyl-1,3,4-thiadiazole,
2-methylsulfinyl-5-propylsulfonyl-1,3,4-thiadiazole,
2-isopropylsulfonyl-5-propylsulfinyl-1,3,4-thiadiazole,
2-butylsulfinyl-5-isopropylsulfonyl-1,3,4-thiadiazole,
2-isobutylsulfinyl-5-isopropylsulfonyl-1,3,4-thiadiazole,
2-hexylsulfinyl-5-isopropylsulfonyl-1,3,4-thiadiazole,
2-isopropylsulfonyl-5-methylsulfinyl-1,3,4-thiadiazole,
2-ethylsulfonyl-5-isopropylsulfinyl-1,3,4-thiadiazole,
2-ethylsulfonyl-5-(1-methylbutylsulfinyl)-1,3,4-thiadiazole,
2-(1-ethylbutylsulfinyl)-5-ethylsulfonyl-1,3,4-thiadiazole,
2-(1-methylbutylsulfinyl)-5-propylsulfonyl-1,3,4-thiadiazole,
2-(1-ethylbutylsulfinyl)-5-propylsulfonyl-1,3,4-thiadiazole,
2-butylsulfonyl-5-(1-methylbutylsulfinyl)-1,3,4-thiadiazole,
2-(1-methylbutylsulfinyl)-5-pentylsulfonyl-1,3,4-thiadiazole,
2-(1-methylbutylsulfinyl-5-(2-methylpropylsulfonyl)-1,3,4-thiadiazole,
2-(1-methylbutylsulfinyl)-5-methylsulfonyl-1,3,4-thiadiazole,
2-(1-ethylbutylsulfinyl)-5-butylsulfonyl-1,3,4-thiadiazole,
2-(1-ethylbutylsulfinyl)-5-pentylsulfonyl-1,3,4-thiadiazole,
2-(1-ethylbutylsulfinyl)-5-propylsulfonyl-1,3,4-thiadiazole,
2-(1-ethylbutylsulfinyl)-5-(2-methylpropylsulfonyl)-1,3,4-thiadiazole,
2-(1-ethylbutylsulfinyl)-5-methylsulfonyl-1,3,4-thiadiazole,
2-methylsulfinyl-5-methylsulfonyl-1,3,4-thiadiazole,
2-methylsulfonyl-5-propylsulfinyl-1,3,4-thiadiazole,
2-isopropylsulfinyl-5-methylsulfonyl-1,3,4-thiadiazole,
2-ethylsulfonyl-5-methylsulfinyl-1,3,4-thiadiazole,
2-ethylsulfonyl-5-propylsulfinyl-1,3,4-thiadiazole,
2-ethylsulfonyl-5-butylsulfinyl-1,3,4-thiadiazole,
2-ethylsulfonyl-5-pentylsulfinyl-1,3,4-thiadiazole,
2-ethylsulfonyl-5-hexylsulfinyl-1,3,4-thiadiazole,
2-ethylsulfonyl-5-isobutylsulfinyl-1,3,4-thiadiazole,
2-ethylsulfonyl-5-sec.-butylsulfinyl-1,3,4-thiadiazole,
2-butylsulfonyl-5-methylsulfinyl-1,3,4-thiadiazole,
2-sec.-butylsulfonyl-5-propylsulfinyl-1,3,4-thiadiazole,
2-sec.-butylsulfonyl-5-isopropylsulfinyl-1,3,4-thiadiazole,
2-ethylsulfonyl-5-tert.-butylsulfinyl-1,3,4-thiadiazole,
2-butylsulfonyl-5-propylsulfinyl-1,3,4-thiadiazole,
2-butylsulfonyl-5-isopropylsulfinyl-1,3,4-thiadiazole,
2-butylsulfinyl-5-butylsulfonyl-1,3,4-thiadiazole,
2-butylsulfonyl-5-isobutylsulfinyl-1,3,4-thiadiazole,
2-butylsulfinyl-5-methylsulfonyl-1,3,4-thiadiazole,
2-tert.-butylsulfinyl-5-methylsulfonyl-1,3,4-thiadiazole,
2-isobutylsulfinyl-5-methylsulfonyl-1,3,4-thiadiazole,
2-tert.-butylsulfinyl-5-butylsulfonyl-1,3,4-thiadiazole,
2-butylsulfonyl-5-pentylsulfinyl-1,3,4-thiadiazole,
2-butylsulfonyl-5-hexylsulfinyl-1,3,4-thiadiazole,
2-hexylsulfinyl-5-methylsulfonyl-1,3,4-thiadiazole,
2-methylsulfonyl-5-pentylsulfinyl-1,3,4-thiadiazole,
2-sec.butylsulfinyl-5-methylsulfonyl-1,3,4-thiadiazole,
2-isopentylsulfinyl-5-methylsulfonyl-1,3,4-thiadiazole, Also there is provided a method for production of 1,3,4-thiadiazole derivatives having a composition of the general formula

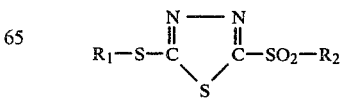

wherein $R_1$ and $R_2$ are independently alkyl with from 1 to 6 carbon atoms, alkenyl with from 2 to 6 carbon atoms, alkinyl with from 2 to 6 carbon atoms or cycloalkyl with from 3 to 6 carbon atoms. A 1,3,4-thiadiazole derivative having a composition of the general formula

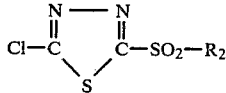

wherein $R_2$ has the same meaning as above, is contacted with a compound having a composition of the general formula

wherein $R_1$ has the same meaning as above, in the presence of organic bases or in the form of their alkali salts. The reaction is not critical to pressure, and is performed at temperatures and times suitable. Preferred are temperatures from about 0° C. to 100° C.

Also there is provided a method for production of 1,3,4-thiadiazole derivatives having a composition of the general formula

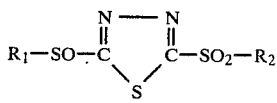

wherein $R_1$ and $R_2$ are independently alkyl with from 1 to 6 carbon atoms, alkenyl with from 2 to 6 carbon atoms, alkinyl with from 2 to 6 carbon atoms or cycloalkyl with from 3 to 6 carbon atoms by contacting 1,3,4-thiadiazole derivatives having a composition of the general formula

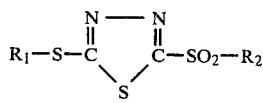

wherein $R_1$ and $R_2$ have the same meaning as above, with oxidants dissolved in an inert solvent. The oxidant can be a member of the group consisting of organic hydroperoxides and peracids or can be an inorganic oxidant. Preferably about stochiometric amounts of the 1,3,4-thiadiazole derivative and of the oxidant are employed. The reaction is not critical to pressure and suitable reaction temperatures and times are used. A preferred temperature range is from about 0° C. to 60° C.

In addition a method is provided for controlling fungi, preferably grain fungi, comprising placing into the surroundings of the fungi a composition comprising 1,3,4-thiadiazole derivatives represented by the general formula

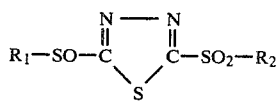

wherein $R_1$ and $R_2$ are independently alkyl with from 1 to 6 carbon atoms, alkenyl with from 2 to 6 carbon atoms, alkinyl with from 2 to 6 carbon atoms or cycloalkyl with from 3 to 6 carbon atoms.

DESCRIPTION OF INVENTION AND PREFERRED EMBODIMENTS

In accordance with the present invention there is provided a material characterized in that it comprises one or more compounds of the general formula

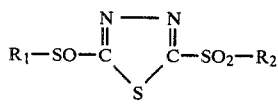

wherein $R_1$ and $R_2$ are the same or are different and in each case mean $C_1$-to $C_6$-alkyl, $C_2$- to $C_6$-alkenyl, $C_2$- to $C_6$-alkinyl or $C_3$- to $C_6$-cycloalkyl. Preferred compounds include those wherein $R_1$ and $R_2$ are alkyl with from 2 to 4 carbon atoms.

Surprisingly, the compounds according to the present invention are much more effective against grain fungi than the known compounds of analog constitution and can be employed with particular advantage for the protection of grain cultures such as barley, oats, rye and wheat against fungi infection.

In addition, these compounds are very effective against leaf and ground fungi and furthermore they have a sufficient chemotherapeutical index.

An additional important advantage comprises, that in comparison with the mercury compounds, which are in fact fungicidal, but which are toxilogically problematical, these compounds a environmentally very acceptable.

Furthermore, the compounds of the present invention are in part superior to preparations known in the art of other constitution, for example manganese ethylenebisdithiocarbamate, N-trichloromethylmercaptotetrahydrophthalimide, 3-trichloromethyl-5-ethoxy-1,2,4-thiadiazole, pentachloronitrobenzene, methyl-1-(butylcarbamoyl)-2-benzimidoazolecarbamate and 3-(3,5-dichlorophenyl)-5-methyl-5-vinyl-1,3-oxazolidine-2,4-dione.

Since the compounds according to the present invention in the amounts practically employed are not phytotoxical when the soil stability is good, they can be employed with large successes for soil and ground treatment.

The fungi well contollable include stem rot and grey mould (*Botyris cinerea*), Septoria leaf or glume blotch (*Leptosphaeria nodorum* [=*Septoria nodorum*]), snow mould and black mould (*Micronectriella nivalis* [=*Fusarium nivale*]), late blight (*Phytophthora infestans*), blast disease (*Piricularia oryzae*), downy mildew (*Plasmopara viticola*), leaf stripe (*Pyrenophora graminea* [=*Helminthosphorium gramineum*]), stinking smut (*Tilletia caries*), rust (*Uromyces appendiculatus* [=*Uromyces phaseoli*]), semiloose smut (*Ustilago avenae*), scab and black spot (*Venturia inaequalis* [=*Fusicladium dentriticum*]) and others.

Among the compounds of the present invention the ones with very good fungicidal effects include those wherein in the formula above $R_1$ and/or $R_2$ are methyl, ethyl, propyl, isopropyl, cyclopropyl, 2-propenyl, 2-propinyl, n-butyl, isobutyl, sec.-butyl, n-pentyl, sec.-pentyl, isopentyl, n-hexyl, sec.-hexyl or isohexyl.

An extraordinary effect is exhibited among these compounds by the following compounds:

2-ethylsulfinyl-5-methylsulfonyl-1,3,4-thiadiazole,
2-ethylsulfinyl-5-ethylsulfonyl-1,3,4-thiadiazole,
2-ethylsulfinyl-5-propylsulfonyl-1,3,4-thiadiazole,
2-ethylsulfinyl-5-butylsulfonyl-1,3,4-thiadiazole, and
2-ethylsulfinyl-5-isopropylsulfonyl-1,3,4-thiadiazole.

The compounds of the present invention can be employed as an agent either solely by themselves or in a mixture among themselves or together with other effective agents. If desired other fungicides, nematicides, insecticides and other pest control agents can be added depending on the desired effect.

Advantageously, the agents are employed in the form of preparations as for example powders, strewing powders, granulates, solutions, emulsions or suspensions and possibly with the addition of liquid and/or solid carrier materials and thinners, respectively and if desired with surface active agents.

Suitable liquid carrier materials include water, mineral oils, and other organic solvents such as for example xylene, chlorobenzene, cyclohexanol, dioxane, acetonitrile, ethylacetate, dimethylformamide, isophorone and dimethylsulfoxide.

As solid carrier materials are suitable lime, kaolin, chalk, talcum, attaclay and other clays as well as natural and synthetic silicon dioxide.

As examples of surface active agents are cited: salts of ligninsulfonic acids, salts of alkylated benzenesulfonic acids, sulfonated organic amides and their salts, polyethoxylated amines and alcohols.

In case the effective agents are to be used for seed treatment, coloring agents can be mixed in for providing a clearly visible color to the treated seeds.

The concentration of the agent or agents, respectively, on the average can vary over a wide range and the concentration of the effective agents depends mainly on the amount in which the preparations are to be applied. For example, the preparations can contain from about 1 to 95 weight percent of active ingredient, and preferably from 20 to 50 percent of active ingredient and about 99 to 5 weight percent of liquid or solid carrier materials as well as up to about 20 weight percent surface active materials.

The application of the materials can be performed as usual, for example by splashing, spraying, atomizing, dusting, gasifying, filling with smoke, dispersing, pouring and treating.

The compounds of the present invention can be prepared for example by reacting compounds of the general formula

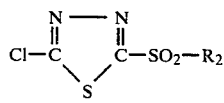

with compounds of the general formula $R_1$—SH in the presence of organic bases or in the form of their alkali salts resulting in formation of compounds of the general formula

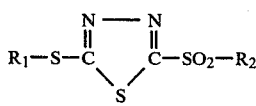

which compounds are then in turn treated with oxidizing agents, preferably hydroperoxides, peracids or inorganic oxidation agents, in about equimolar amounts and dissolved in an inert solvent. $R_1$ and $R_2$ have the same meaning as indicated above.

The cited 2-chloro-5-sulfonyl-1,3,4-thiadiazol derivatives are prepared by methods in themselves known. In the further reaction with alkylthiols the organic bases employable include pyridine, 4-dimethylaminopyridine or 4-pyrrolidinopyridine and tertiary amines, for example triethylamine or N,N-dimethylaniline. The alkali salts preferred are those of sodium and potassium.

For sulfoxidation, the organic oxidizing agents employable include hydroperoxides such as tert.-butylhydroperoxide, or peracids such as m-chloroperbenzoic acid, or N-halo-carbonic acid amides such as N-bromosuccinimide.

Just as well inorganic oxidizing agents can be employed such as hydrogen peroxide or sodium metaperiodate. For each one mole of the thio compound two oxidation equivalents are employed.

In general the reactions are performed in the range from about 0° C. to the boiling points of the solvents employed. For sulfoxidation the reaction temperature should not surpass 60° C. The reactants are employed in about equimolar amounts for the synthesis of the compounds of the present invention.

Suitable as reaction media are solvents inert with respect to the reactants. Their selection depends on generally known considerations relating to the purpose of the reaction to be performed.

Suitable solvents include carbonic acids such as acetic acid, carbonic acid amides such as dimethylformamide, carbonic acid nitriles such as acetonitrile, alcohols such as methanol, ethanol, ethers such as diethylether, dioxane and many others.

The isolation of the compounds formed in accordance with the present invention can be achieved by distillation of the solvent employed at atmospheric or reduced pressure or by precipitation with water when hydrophilic solvents are employed and finally by crystallization.

The following examples illustrate the preparation of the compounds of the present invention.

EXAMPLE 1

2-Ethylsulfinyl-5-butylsulfonyl-1,3,4-thiadiazole

A solution of 53.29 g of 2-Ethylthio-5-butylsulfonyl-1,3,4-thiadiazole in 500 ml acetic acid is mixed with 23 g of 30 percent hydrogen peroxide. The reaction takes place over night upon standing at room temperature. Then one liter water is added to the reaction solution, the separated oil is extracted with dichloromethane, the extract is freed from acetic acid by extraction with soda ash solution, the dichloromethane phase is dried with magnesium sulfate and the solvent is distilled off completely, finally in vacuo. The remaining residue is recrystallized from isopropylether/isopropanol.

Yield: 48.9 g = 87 percent of theory
Fp.: 43° C.

EXAMPLE 2

2-Isopropylsulfinyl-5-isopropylsulfonyl-1,3,4-thiadiazole 13.3 g 2-isopropylthio-5-isopropylsulfonyl-1,3,4-thiadiazole are dissolved in 50 ml dichloromethane and to the solution is added drop by drop at 10° to 15° C. under agitation and cooling a solution of 8.63 g m-chloroperbenzoic acid in 200 ml dichloromethane. The reaction mixture is stirred for another thirty minutes, then extracted with aqueous soda ash solution for removing the m-chlorobenzoic acid, the organic phase is separated and dried with magnesium sulfate. After distilling off the solvent a residue is obtained, which is recrystallized from acetonitrile.

Yield: 12.0 g = 85 percent of theory
Fp.: 165° C. (decomposition).

Similarly the compounds according to the present invention and listed in the following table are prepared.

| Name of compound | Physical constant |
| --- | --- |
| 2-Ethylsulfinyl-5-methylsulfonyl-1,3,4-thiadiazole | Fp.: 75° C. |
| 2-Ethylsulfinyl-5-ethylsulfonyl-1,3,4-thiadiazole | Fp.: 61° C. |
| 2-Ethylsulfinyl-5-propylsulfonyl-1,3,4-thiadiazole | Fp.: 38° C. |
| 2-Ethylsulfinyl-5-isopropylsulfonyl-1,3,4-thiadiazole | Fp.: 118° C. |
| 2-Ethylsulfinyl-5-sec.-butylsulfonyl-1,3,4-thiadiazole | $n_D^{20}$ 1.5361 |
| 2-Methylsulfinyl-5-propylsulfonyl-1,3,4-thiadiazole | Fp.: 87° C. |
| 2-Isopropylsulfonyl-5-propylsulfinyl-1,3,4-thiadiazole | Fp.: 78° C. |
| 2-Butylsulfinyl-5-isopropylsulfonyl-1,3,4-thiadiazole | Fp.: 66° C. |
| 2-Isobutylsulfinyl-5-isopropylsulfonyl-1,3,4-thiadiazole | Fp.: 93° C. |
| 2-Hexylsulfinyl-5-isopropylsulfonyl-1,3,4-thiadiazole | $n_D^{20}$: 1.5375 |
| 2-Isopropylsulfonyl-5-methylsulfinyl-1,3,4-thiadiazole | Fp.: 64° C. |
| 2-Ethylsulfonyl-5-isopropylsulfinyl-1,3,4-thiadiazole | Fp.: 99° C. |
| 2-Ethylsulfonyl-5-(1-methylbutylsulfinyl)-1,3,4-thiadiazole | $n_D^{20}$: 1.5299 |
| 2-(1-Ethylbutylsulfinyl)-5-ethylsulfonyl-1,3,4-thiadiazole | $n_D^{20}$: 1.5284 |
| 2-(1-Methylbutylsulfinyl)-5-propylsulfonyl-1,3,4-thiadiazole | $n_D^{20}$: 1.5288 |
| 2-(1-Ethylbutylsulfinyl)-5-propylsulfonyl-1,3,4-thiadiazole | $n_D^{20}$: 1.5249 |
| 2-Butylsulfonyl-5-(1-methylbutylsulfinyl)-1,3,4-thiadiazole | $n_D^{20}$: 1.5222 |
| 2-(1-Methylbutylsulfinyl)-5-pentylsulfonyl-1,3,4-thiadiazole | $n_D^{20}$: 1.5195 |
| 2-(1-Methylbutylsulfinyl)-5-(2-methylpropylsulfonyl)-1,3,4-thiadiazole | $n_D^{20}$: 1.5222 |
| 2-(1-Methylbutylsulfinyl)-5-methylsulfonyl-1,3,4-thiadiazole | $n_D^{20}$: 1.5280 |
| 2-(1-Ethylbutylsulfinyl)-5-butylsulfonyl-1,3,4-thiadiazole | $n_D^{20}$: 1.5173 |
| 2-(1-Ethylbutylsulfinyl)-5-pentylsulfonyl-1,3,4-thiadiazole | $n_D^{20}$: 1.5128 |
| 2-(1-Ethylbutylsulfinyl)-5-propylsulfonyl-1,3,4-thiadiazole | $n_D^{20}$: 1.5168 |
| 2-(1-Ethylbutylsulfinyl)-5-(2-methylpropylsulfonyl)-1,3,4-thiadiazole | $n_D^{20}$: 1.5150 |
| 2-(1-Ethylbutylsulfinyl)-5-methylsulfonyl-1,3,4-thiadiazole | $n_D^{20}$: 1.5220 |
| 2-Methylsulfinyl-5-methylsulfonyl-1,3,4-thiadiazole | Fp.: 145° C. |
| 2-Methylsulfonyl-5-propylsulfinyl-1,3,4-thiadiazole | Fp.: 62° C. |
| 2-Isopropylsulfinyl-5-methylsulfonyl-1,3,4-thiadiazole | Fp.: 63° C. |
| 2-Ethylsulfonyl-5-methylsulfinyl-1,3,4-thiadiazole | Fp.: 93° C. |
| 2-Ethylsulfonyl-5-propylsulfinyl-1,3,4-thiadiazole | Fp.: 63° C. |
| 2-Ethylsulfonyl-5-butylsulfinyl-1,3,4-thiadiazole | Fp.: 52° C. |
| 2-Ethylsulfonyl-5-pentylsulfinyl-1,3,4-thiadiazole | $n_D^{20}$: 1.5488 |
| 2-Ethylsulfonyl-5-hexylsulfinyl-1,3,4-thiadiazole | $n_D^{20}$: 1.5420 |
| 2-Ethylsulfonyl-5-isobutylsulfinyl-1,3,4-thiadiazole | Fp.: 71° C. |
| 2-Ethylsulfonyl-5-sec.-butylsulfinyl-1,3,4-thiadiazole | Fp.: 76° C. |
| 2-Butylsulfonyl-5-methylsulfinyl-1,3,4-thiadiazole | Fp.: 63° C. |
| 2-sec.-Butylsulfonyl-5-propylsulfinyl-1,3,4-thiadiazole | $n_D^{20}$: 1.5508 |
| 2-sec.-Butylsulfonyl-5-isopropylsulfinyl-1,3,4-thiadiazole | Fp.: 92° C. |
| 2-Ethylsulfonyl-5-tert.-butylsulfinyl-1,3,4-thiadiazole | Fp.: 112° C. (decomp.) |
| 2-Butylsulfonyl-5-propylsulfinyl-1,3,4-thiadiazole | Fp.: 43° C. |
| 2-Butylsulfonyl-5-isopropylsulfinyl-1,3,4-thiadiazole | Fp.: 62° C. |
| 2-Butylsulfinyl-5-butylsulfonyl-1,3,4-thiadiazole | Fp.: 68° C. |
| 2-Butylsulfonyl-5-isobutylsulfinyl-1,3,4-thiadiazole | Fp.: 73° C. |
| 2-Butylsulfinyl-5-methylsulfonyl-1,3,4-thiadiazole | Fp.: 56° C. |
| 2-tert.-Butylsulfinyl-5-methylsulfonyl-1,3,4-thiadiazole | Fp.: 108° C. (decomp.) |
| 2-Isobutylsulfinyl-5-methylsulfonyl-1,3,4-thiadiazole | Fp.: 106° C. |
| 2-tert.-Butylsulfinyl-5-butylsulfonyl-1,3,4-thiadiazole | Fp.: 62° C. |
| 2-Butylsulfonyl-5-pentylsulfinyl-1,3,4-thiadiazole | Fp.: 52° C. |
| 2-Butylsulfonyl-5-hexylsulfinyl-1,3,4-thiadiazole | Fp.: 52° C. |
| 2-Hexylsulfinyl-5-methylsulfonyl-1,3,4-thiadiazole | Fp.: 65° C. |
| 2-Methylsulfonyl-5-pentylsulfinyl-1,3,4-thiadiazole | Fp.: 75° C. |
| 2-sec.-Butylsulfinyl-5-methylsulfonyl-1,3,4-thiadiazole | Fp.: 84° C. |
| 2-Isopentylsulfinyl-5-methylsulfonyl-1,3,4-thiadiazole | Fp.: 73° C. |

The compounds according to the present invention are colorless and odorless stabile oils or crystalline bodies, which are insoluble in water, little soluble in lower hydrocarbons, however which are well soluble in organic solvents as usually employed such as carbonic acids, carbonic acid amides, carbonic acid esters, alcohols, ethers and the like.

The starting materials for preparing the compounds of the present invention can be prepared by the following methods.

EXAMPLE 3

2-Ethylthio-5-butylsulfonyl-1,3,4-thiadiazole 114.5 g 2-butylsulfonyl-5-chloro-1,3,4-thiadiazole and 36 ml ethylmercaptan are dissolved in 400 ml dioxane. Then under agitation 70 ml triethylamine are added to this drop by drop and the solution is heated to boiling under reflux for about one hour. After cooling the reaction mixture is introduced into ice water, the separating oil is extracted with dichloromethane, the methylenechloride phase is dried with magnesiumsulfate and the solvent is completely distilled off, finally in vacuo. 125.3 g of a colorless oil, that is 99 percent of theory, are obtained with an index of refraction of $n_D^{20} = 1.5552$.

Similarly the starting and intermediate products, respectively, are prepared as listed in the following table.

| Name of compound | Physical constant |
|---|---|
| 2-Ethylthio-5-methylsulfonyl-1,3,4-thiadiazole | Fp.: 78° C. |
| 2-Ethylthio-5-propylsulfonyl-1,3,4-thiadiazole | Fp.: 36° C. |
| 2-Ethylthio-5-sec.-butylsulfonyl-1,3,4-thiadiazole | $n_D^{20}$: 1.5401 |
| 2-Ethylthio-5-isopropylsulfonyl-1,3,4-thiadiazole | Fp.: 42° C. |
| 2-Isopropylsulfonyl-5-propylthio-1,3,4-thiadiazole | Fp.: 31° C. |
| 2-Isopropylsulfonyl-5-isopropylthio-1,3,4-thiadiazole | Fp.: 48° C. |
| 2-Isobutylthio-5-isopropylsulfonyl-1,3,4-thiadiazole | $n_D^{20}$: 1.5490 |
| 2-Butylthio-5-isopropylsulfonyl-1,3,4-thiadiazole | $n_D^{20}$: 1.5490 |
| 2-Hexylthio-5-isopropylsulfonyl-1,3,4-thiadiazole | $n_D^{20}$: 1.5420 |
| 2-Ethylsulfonyl-5-isopropylthio-1,3,4-thiadiazole | $n_D^{20}$: 1.5653 |
| 2-Methylsulfonyl-5-methylthio-1,3,4-thiadiazole | Fp.: 67° C. |
| 2-Methylsulfonyl-5-propylthio-1,3,4-thiadiazole | Fp.: 47° C. |
| 2-Isopropylthio-5-methylsulfonyl-1,3,4-thiadiazole | Fp.: 36° C. |
| 2-Ethylsulfonyl-5-methylthio-1,3,4-thiadiazole | Fp.: 50° C. |
| 2-Ethylsulfonyl-5-propylthio-1,3,4-thiadiazole | $n_D^{20}$: 1.5692 |
| 2-Ethylsulfonyl-5-butylthio-1,3,4-thiadiazole | $n_D^{20}$: 1.5600 |
| 2-Ethylsulfonyl-5-pentylthio-1,3,4-thiadiazole | $n_D^{20}$: 1.5552 |
| 2-Ethylsulfonyl-5-hexylthio-1,3,4-thiadiazole | $n_D^{20}$: 1.5481 |
| 2-Ethylsulfonyl-5-isobutylthio-1,3,4-thiadiazole | $n_D^{20}$: 1.5616 |
| 2-Ethylsulfonyl-5-sec.-butylthio-1,3,4-thiadiazole | $n_D^{20}$: 1.5630 |
| 2-sec.-Butylsulfonyl-5-propylthio-1,3,4-thiadiazole | $n_D^{20}$: 1.5542 |
| 2-sec.-Butylsulfonyl-5-isopropylthio-1,3,4-thiadiazole | $n_D^{20}$: 1.5457 |
| 2-Ethylsulfonyl-5-tert.-butylthio-1,3,4-thiadiazole | $n_D^{20}$: 1.5575 |
| 2-Butylthio-5-methylsulfonyl-1,3,4-thiadiazole | $n_D^{20}$: 1.5687 |
| 2-tert.-butylthio-5-methylsulfonyl-1,3,4-thiadiazole | $n_D^{20}$: 1.5633 |
| 2-Isobutylthio-5-methylsulfonyl-1,3,4-thiadiazole | Fp.: 54° C. |
| 2-Methylsulfonyl-5-pentylthio-1,3,4-thiadiazole | $n_D^{20}$: 1.5614 |
| 2-Hexylthio-5-methylsulfonyl-1,3,4-thiadiazole | $n_D^{20}$: 1.5542 |
| 2-Butylsulfonyl-5-methylthio-1,3,4-thiadiazole | $n_D^{20}$: 1.5772 |
| 2-Butylsulfonyl-5-propylthio-1,3,4-thiadiazole | $n_D^{20}$: 1.5551 |
| 2-Butylsulfonyl-5-isopropylthio-1,3,4-thiadiazole | $n_D^{20}$: 1.5533 |
| 2-Butylsulfonyl-5-butylthio-1,3,4-thiadiazole | Fp.: 40° C. |
| 2-Isopentylthio-5-methylsulfonyl-1,3,4-thiadiazole | $n_D^{20}$: 1.5620 |

These materials are again stabile oils or crystalline bodies. They dissolve well in carbonic acids, carbonic acid amides, carbonic acid esters, alcohols, ketones, ethers and are insoluble in water.

The following examples are intended to illustrate the superior activity and possibilities of application of the compounds of the present invention, which is provided by its forms of preparations.

EXAMPLE 4

Test of concentration limit in the control of root rot (*Pythium ultimum*)

20 percent active ingredient containing powder preparations were uniformly mixed with the soil, which was strongly contaminated with root rot (*Pythium ultimum*). The treated soil was filled in clay dishes capable of holding 0.5 liter of soil and without waiting 20 grains of peas (*Pisum sativum L.* convar. medullare Alef.) of the variety "Marvel of Kelvedon" were sowed into each dish. After a culture time of three weeks at 20° to 24° C. in a green house the number of healthy peas was determined and a root evaluation was performed.

Active agents, amounts and results are listed in the following table.

Root evaluation:
4 = white roots, without fungus necrosis;
3 = white roots, slight fungus necrosis;
2 = brown roots, already considerable fungus necrosis;
1 = strong fungus necrosis, roots rotted.

TEST OF CONCENTRATION LIMIT IN THE CONTROL OF ROOT ROT (*PYTHIUM ULTIMUM*)

| Compounds according to the present invention | Active ingredient Concentration mg/liter of soil | Number of healthy peas | Root evaluation (1–4) |
|---|---|---|---|
| 2-Ethylsulfinyl-5-methylsulfonyl-1,3,4-thiadiazole | 20 mg | 17 | 4 |
| | 40 mg | 18 | 4 |
| | 80 mg | 19 | 4 |
| 2-Ethylsulfinyl-5-ethylsulfonyl-1,3,4-thiadiazole | 20 mg | 18 | 4 |
| | 40 mg | 19 | 4 |
| | 80 mg | 19 | 4 |
| 2-Ethylsulfinyl-5-propylsulfonyl-1,3,4-thiadiazole | 20 mg | 6 | 1 |
| | 40 mg | 20 | 4 |
| | 80 mg | 19 | 4 |
| 2-Ethylsulfinyl-5-isopropylsulfonyl-1,3,4-thiadiazole | 20 mg | 17 | 3 |
| | 40 mg | 18 | 4 |
| | 80 mg | 18 | 4 |
| 2-Ethylsulfinyl-5-sec.-butylsulfonyl-1,3,4-thiadiazole | 20 mg | 8 | 2 |
| | 40 mg | 15 | 4 |
| | 80 mg | 15 | 4 |
| 2-Methylsulfinyl-5-propylsulfonyl-1,3,4-thiadiazole | 20 mg | 6 | 1 |
| | 40 mg | 8 | 1 |
| | 80 mg | 17 | 4 |
| 2-Ethylsulfinyl-5-butylsulfonyl-1,3,4-thiadiazole | 20 mg | 12 | 2 |
| | 40 mg | 18 | 4 |
| | 80 mg | 17 | 4 |
| 2-Ethylsulfonyl-5-isopropylsulfinyl-1,3,4-thiadiazole | 20 mg | 17 | 4 |
| | 40 mg | 18 | 4 |
| | 80 mg | 17 | 4 |
| 2-Isopropylsulfonyl-5-propylsulfinyl-1,3,4-thiadiazole | 20 mg | 13 | 1 |
| | 40 mg | 15 | 3 |
| | 80 mg | 15 | 4 |
| 2-Butylsulfinyl-5-isopropylsulfonyl-1,3,4-thiadiazole | 20 mg | 8 | 1 |
| | 40 mg | 14 | 2 |
| | 80 mg | 17 | 4 |
| 2-Isobutylsulfinyl-5-isopropylsulfonyl-1,3,4-thiadiazole | 20 mg | 8 | 1 |
| | 40 mg | 8 | 1 |
| | 80 mg | 17 | 4 |
| COMPARISON AGENTS | | | |
| Manganese-ethylene-1,2-bisdithiocarbamate | 20 mg | 4 | 1 |
| | 40 mg | 5 | 1 |
| | 80 mg | 10 | 2 |
| N-Trichloromethylmercapto-tetrahydro-phthalimide | 20 mg | 2 | 1 |
| | 40 mg | 2 | 1 |
| | 80 mg | 9 | 2 |
| Control I (3 repititions) | — | 0 | 1 |
| Contaminated soil without treatment | — | 1 | 1 |
| Control II (3 repititions) | — | 0 | 1 |
| | — | 18 | 4 |

| TEST OF CONCENTRATION LIMIT IN THE CONTROL OF ROOT ROT (*PYTHIUM ULTIMUM*) | | | |
|---|---|---|---|
| Compounds according to the present invention | Active ingredient Concentration mg/liter of soil | Number of healthy peas | Root evaluation (1–4) |
| Steamed soil | — | 20 | 4 |
| | — | 19 | 4 |

EXAMPLE 5

Test of concentration limit in the control of Fusarium root rot (*Fusarium avenaceum*)

A 20 percent active ingredient powder preparation was uniformly mixed with soil, which was strongly contaminated with Fusarium root rot (*Fusarium avenaceum*). The treated soil was filled into clay dishes capable of holding 0.5 liter soil and 20 grains of peas (*Pisum sativum L.* convar. medullare Alf.) of the variety "Marvel of Kelvedon" were sowed into each dish without waiting. After a culture time of 18 days at 20° to 24° C. in a green house the number of healthy peas was determined and a root evaluation (1–4) was performed.

Active ingredients, amounts employed and results are listed in the following table.

Root evaluation:
4 = white roots, without fungus necrosis;
3 = white roots, slight fungus necrosis;
2 = brown roots, already considerable fungus necrosis;
1 = strong fungus necrosis, roots rotted.

| TEST OF CONCENTRATION LIMIT IN THE CONTROL OF FUSARIUM ROOT ROT (*FUSARIUM AVENACEUM*) | | | |
|---|---|---|---|
| Compounds according to the present invention | Active ingredient concentration mg/liter soil | Number of healthy peas | Root evaluation (1–4) |
| 2-Ethylsulfonyl-5-isopropyl-sulfinyl-1,3,4-thiadiazole | 25 mg | 14 | 4 |
| | 50 mg | 18 | 4 |
| | 100 mg | 18 | 4 |
| 2-Isopropylsulfonyl-5-methyl-sulfinyl-1,3,4-thiadiazole | 25 mg | 14 | 2 |
| | 50 mg | 19 | 4 |
| | 100 mg | 19 | 4 |
| 2-Ethylsulfinyl-5-ethyl-sulfonyl-1,3,4-thiadiazole | 25 mg | 12 | 3 |
| | 50 mg | 19 | 4 |
| | 100 mg | 19 | 4 |
| 2-Ethylsulfinyl-5-propyl-sulfonyl-1,3,4-thiadiazole | 25 mg | 17 | 3 |
| | 50 mg | 19 | 4 |
| | 100 mg | 20 | 4 |
| 2-Ethylsulfinyl-5-isopropyl-sulfonyl-1,3,4-thiadiazole | 25 mg | 8 | 1 |
| | 50 mg | 16 | 3 |
| | 100 mg | 17 | 4 |
| 2-Ethylsulfinyl-5-butyl-sulfonyl-1,3,4-thiadiazole | 25 mg | 11 | 2 |
| | 50 mg | 18 | 4 |
| | 100 mg | 16 | 4 |
| 2-Hexylsulfinyl-5-isopropyl-sulfonyl-1,3,4-thiadiazole | 25 mg | 6 | 2 |
| | 50 mg | 14 | 4 |
| | 100 mg | 16 | 4 |
| 2-Isopropylsulfonyl-5-propyl-sulfinyl-1,3,4-thiadiazole | 25 mg | 11 | 2 |
| | 50 mg | 11 | 3 |
| | 100 mg | 17 | 4 |
| 2-Methylsulfinyl-5-propyl-sulfonyl-1,3,4-thiadiazole | 25 mg | 3 | 1 |
| | 50 mg | 14 | 3 |
| | 100 mg | 18 | 4 |
| 2-Ethylsulfinyl-5-sec.-butyl-sulfonyl-1,3,4-thiadiazole | 25 mg | 5 | 1 |
| | 50 mg | 13 | 2 |
| | 100 mg | 16 | 4 |
| 2-Ethylsulfinyl-5-methyl-sulfonyl-1,3,4-thiadiazole | 25 mg | 4 | 2 |
| | 50 mg | 7 | 3 |
| | 100 mg | 16 | 4 |
| COMPARISON AGENTS | | | |
| 3-Trichloromethyl-5-ethoxy-1,3,4-thiadiazole | 25 mg | 0 | 1 |
| | 50 mg | 0 | 1 |
| | 100 mg | 0 | 1 |
| Manganese ethylene-1,2-bisdithiocarbamate | 25 mg | 0 | 1 |
| | 50 mg | 0 | 1 |
| | 100 mg | 11 | 1 |
| Control I (3 repititions) | — | 0 | 1 |
| Contaminated soil without treatment | — | 0 | 1 |
| | — | 0 | 1 |
| Control II (3 repititions) | — | 18 | 4 |
| Steamed soil | — | 19 | 4 |
| | — | 18 | 4 |

EXAMPLE 6

Retardation of fungus growth on nutritive broth 20 ml of a nutritive broth from grape juice and water (1:1) were filled in a glass flask capable of holding 100 ml and the active ingredient preparations in powder form were added. Then the solution was inoculated with conidium (spores) or sclerotium of the test fungi. After a breeding time of 6 days at 21° C. to 23° C. the development of the fungi was evaluated on the surface of the nutritive broth.

Test fungi: blue mould (*Pennicillium digitatum*), grey mould (*Botrytis cinerea*), Alternaria leaf spot (*Alternaria solani*), Fusarium root rot (*Fusarium avenaceum*), basal sheath rot (*Corticium rolfsii*).

Evaluation:
0 = no fungi growth
1 = individual fungi colonies on the surface
2 = surface 5–10 percent covered with fungi lawn
3 = surface 10–30 percent covered with fungi lawn
4 = surface 30–60 percent covered with fungi lawn
5 = surface 60–100 percent covered with fungi lawn Active ingredients, active ingredient concentration in the nutritive broth and results are listed in the following table.

| Retardation of fungus growth on nutritive broth | | | | | | |
|---|---|---|---|---|---|---|
| Compounds according to the present invention | Active agent concentration in the nutritive solution | Penicillium digitatum | Botrytis cinerea | Alternaria solani | Fusarium avenaceum | Corticium rolfsii |
| 2-Ethylsulfinyl-5-ethyl-sulfonyl-1,3,4-thiadiazole | 0.002% | 0 | 1 | 0 | 0 | 1 |
| | 0.004% | 0 | 0 | 0 | 0 | 0 |
| 2-Ethylsulfinyl-5-propyl-sulfonyl-1,3,4-thiadiazole | 0.002% | 1 | 1 | 0 | 0 | 0 |
| | 0.004% | 0 | 0 | 0 | 0 | 0 |
| 2-Ethylsulfinyl-5-butyl-sulfonyl-1,3,4-thiadiazole | 0.002% | 1 | 1 | 0 | 0 | 1 |
| | 0.004% | 0 | 0 | 0 | 0 | 0 |
| 2-Ethylsulfinyl-5-isopropyl- | 0.002% | 1 | 2 | 0 | 0 | 1 |

-continued

Retardation of fungus growth on nutritive broth

| Compounds according to the present invention | Active agent concentration in the nutritive solution | Penicillium digitatum | Botrytis cinerea | Alternaria solani | Fusarium avenaceum | Corticium rolfsii |
|---|---|---|---|---|---|---|
| sulfonyl-1,3,4-thiadiazole | 0.004% | 0 | 1 | 0 | 0 | 0 |
| 2-Ethylsulfinyl-5-sec.-butyl- | 0.002% | 1 | 1 | 0 | 0 | 1 |
| sulfonyl-1,3,4-thiadiazole | 0.004% | 0 | 0 | 0 | 0 | 0 |
| 2-Isopropylsulfonyl-5-propyl- | 0.002% | 1 | 1 | 0 | 0 | 1 |
| sulfinyl-1,3,4-thiadiazole | 0.004% | 0 | 0 | 0 | 0 | 1 |
| 2-Methylsulfinyl-5-propyl- | 0.002% | 1 | 1 | 0 | 0 | 1 |
| sulfonyl-1,3,4-thiadiazole | 0.004% | 0 | 0 | 0 | 0 | 1 |
| Comparison preparations | | | | | | |
| Methyl-1-(butylcarbamoyl)-2- | 0.002% | 5 | 0 | 5 | 0 | 5 |
| benzimidazole-carbamate | 0.004% | 5 | 0 | 5 | 0 | 5 |
| 3-(3,5-Dichlorophenyl)-5-methyl- | 0.002% | 3 | 0 | 4 | 5 | 5 |
| 5-vinyl-1,3-oxazolidine-2,4-dione | 0.004% | 3 | 0 | 4 | 5 | 5 |
| Control | — | 5 | 5 | 5 | 5 | 5 |

EXAMPLE 7

Test of concentration limit in the control of Rhizoctonia root and stem rot (*Rhizoctonia solani*)

20 percent active ingredient preparations in powder form were uniformly mixed with soil, which was strongly contaminated by Rhizoctonia root and stem rot (*Rhizoctonia solani*). The soil treated was filled into clay dishes capable of holding 1 liter soil and in each dish 25 grains of peas (*Pisum sativum L.* convar. medullare Alef.) of the variety "Marvel of Kelvedon" were sowed without waiting. After a culturing time of 18 days at 20° to 24° C. in a green house the number of healthy peas was determined and a root evaluation was performed.

Active ingredients, amounts employed and results are listed in the following table.

Root evaluation:
4=white roots, without fungus necrosis;
3=white roots, slight fungus necrosis;
2=brown roots, already considerable fungus necrosis;
1=strong fungus necrosis, roots rotted.

Test of concentration limit in the control of Rhizoctonic root and stem rot(*Rhizoctonia solani*)

| Compounds according to invention | Active ingredient concentration in mg/liter soil | % healthy peas from the seed | Root evaluation (1–4) |
|---|---|---|---|
| 2-(1-Ethylbutylsulfinyl)-5-butylsulfonyl-1,3,4-thiadiazole | 50 mg | 96% | 3 |
|  | 100 mg | 100% | 4 |
| 2-(1-Methylbutylsulfinyl)-5-propylsulfonyl-1,3,4-thiadiazole | 50 mg | 84% | 3 |
|  | 100 mg | 100% | 4 |
| 2-(1-Ethylbutylsulfinyl)-5-(2-methylpropylsulfonyl)-1,3,4-thiadiazole | 50 mg | 80% | 3 |
|  | 100 mg | 100% | 4 |
| 2-(1-Ethylbutylsulfinyl)-5-propylsulfonyl-1,3,4-thiadiazole | 50 mg | 68% | 2 |
|  | 100 mg | 92% | 3 |
| COMPARISON PREPARATIONS | | | |
| Pentachloronitrobenzene | 50 mg | 24% | 1 |
|  | 100 mg | 60% | 3 |
| 3-Trichloromethyl-5-ethoxy-1,2,4-thiadiazole | 50 mg | 20% | 1 |
|  | 100 mg | 64% | 1 |
| Control I Contaminated soil without treatment | — | 8% | 1 |
| Control II Steamed soil | — | 100% | 4 |

EXAMPLE 8

Control of leaf blast (*Pythium splendens*) in the nursery plant growth of geranium (*Pelargonium peltatum*) by watering with activated water Clay dishes with a diameter of 6 cm were filled with the contaminated substrate (peat-sand mixture 1:1) and for each dish 30 ml of the concentration given were added as an aqueous solution. Then nursey plants of the variety "Luisenhof" were planted, for each concentration 12 sprouts without roots. After a time for putting out roots of four weeks in the nursery patch at a substrate temperature of 23° C. the evaluation was performed.

Active ingredients, amounts employed and results are listed in the following table.

Control of leaf blast (*Pythium splendens*) in the nursery plant growth of geranium (*Pelargonium peltatum*) by watering with water containing active ingredients.

| Compound according to invention | Concentration of active ingredient | Plant loss from *Pythium splendens* | Average plant fresh weight |
|---|---|---|---|
| 2-Ethylsulfinyl-5-propylsulfonyl-1,3,4-thiadiazole | 0.0025% | 8% | 8.4 g |
|  | 0.005% | 8% | 9.1 g |
|  | 0.01% | 0% | 8.7 g |
|  | 0.02% | 0% | 8.9 g |
| 2-Ethylsulfinyl-5-butylsulfonyl-1,3,4-thiadiazole | 0.0025% | 0% | 10.5 g |
|  | 0.005% | 0% | 8.8 g |
|  | 0.01% | 0% | 9.4 g |
|  | 0.02% | 0% | 9.1 g |
| 2-Ethylsulfinyl-5-isopropylsulfonyl-1,3,4-thiadiazole | 0.0025% | 0% | 9.5 g |
|  | 0.005% | 0% | 8.8 g |
|  | 0.01% | 0% | 8.0 g |
|  | 0.02% | 0% | 7.3 g |
| Control I Contaminated substrate | | 92% | 7.5 g |

| Control of leaf blast (*Pythium splendens*) in the nursery plant growth of geranium (*Pelargonium peltatum*) by watering with water containing active ingredients. | | | |
|---|---|---|---|
| Compound according to invention | Concentration of active ingredient | Plant loss from *Pythium splendens* | Average plant fresh weight |
| without treatment Control II Steamed substrate | | 0% | 8.3 g |

EXAMPLE 9

Effect of prophylactic leaf treatment against downy mildew (*Plasmora viticola*) at grape vine plants in the green house Young grape vine plants with about from 5 to 8 leaves were splashed dripping wet with the indicated active ingredient concentration, after drying of the wet layer the leaves were sprayed on their bottom side with an aqueous suspension of sporagium of the downy mildew (about 20,000 per ml) and immediately incubated in the greenhouse at 22° C. to 24° C. and at an atmosphere saturated with water vapor as possible. From the second day on the air moisture was taken back to normal size (30 to 70 percent of saturation) and then again kept for a day at water vapor saturation.

Following from each leaf the percentage part ot the area attacked by fungi was determined and the average for each treatment for determining the fungicidal effectiveness was calculated as follows:

$$100 - \left(100 \times \frac{\text{Attack area in treated}}{\text{Attack area in untreated}}\right) = \% \text{ Effectiveness}$$

The compounds of the present invention were formulated as 20% spraypowder.

| Compounds according to invention | % Effectiveness after treatment with 0.025% active ingredient |
|---|---|
| 2-Isopropylsulfonyl-5-isopropylsulfinyl-1,3,4-thiadiazole | 99 |
| 2-Ethylsulfinyl-5-methylsulfonyl-1,3,4-thiadiazole | 91 |
| 2-Ethylsulfinyl-5-propylsulfonyl-1,3,4-thiadiazole | 91 |
| 2-Ethylsulfinyl-5-isopropylsulfonyl-1,3,4-thiadiazole | 100 |
| 2-Butylsulfinyl-5-isopropylsulfonyl-1,3,4-thiadiazole | 99 |
| 2-Isobutylsulfinyl-5-isopropylsulfonyl-1,3,4-thiadiazole | 100 |
| 2-Hexylsulfinyl-5-isopropylsulfonyl-1,3,4-thiadiazole | 98 |
| 2-Isopropylsulfonyl-5-methylsulfinyl-1,3,4-thiadiazole | 90 |
| 2-Ethylsulfonyl-5-(1-methylbutylsulfinyl)-1.3.4-thiadiazole | 99 |
| 2-(1-Ethylbutylsulfinyl)-5-ethylsulfonyl-1,3,4-thiadiazole | 100 |
| 2-(1-Methylbutylsulfinyl)-5-propylsulfonyl-1,3,4-thiadiazole | 94 |
| 2-(1-Ethylbutylsulfinyl)-5-propylsulfonyl-1,3,4-thiadiazole | 100 |
| 2-Butylsulfonyl-5-(1-methylbutylsulfinyl)-1,3,4-thiadiazole | 100 |
| 2-(1-Methylbutylsulfinyl)-5-pentysulfonyl-1,3,4-thiadiazole | 100 |
| 2-(1-Methylbutylsulfinyl)-5-(2-methylpropylsulfonyl)-1,3,4-thiadiazole | 99 |
| 2-(1-Methylbutylsulfinyl)-5-methylsulfonyl-1,3,4-thiadiazole | 100 |
| 2-(1-Ethylbutylsulfinyl)-5-butylsulfonyl-1,3,4-thiadiazole | 100 |
| 2-(1-Ethylbutylsulfinyl)-5-pentylsulfonyl-1,3,4-thiadiazole | 100 |
| 2-(1-Ethylbutylsulfinyl)-5-propylsulfonyl-1,3,4-thiadiazole | 100 |
| 2-(1-Ethylbutylsulfinyl)-5-(2-methylpropylsulfonyl)-1,3,4-thiadiazole | 100 |
| 2-(1-Ethylbutylsulfinyl)-5-methylsulfonyl-1.3.4-thiadiazole | 90 |
| 2-Ethylsulfonyl-5-isopropylsulfinyl-1,3,4-thiadiazole | 89 |
| 2-Methylsulfinyl-5-methylsulfonyl-1,3,4-thiadiazole | 97 |
| 2-Methylsulfonyl-5-propylsulfinyl-1,3,4-thiadiazole | 98 |
| 2-Isopropylsulfinyl-5-methylsulfonyl-1,3,4-thiadiazole | 98 |
| 2-Ethylsulfonyl-5-propylsulfinyl-1,3,4-thiadiazole | 80 |
| 2-Ethylsulfonyl-5-butylsulfinyl-1,3,4-thiadiazole | 80 |
| 2-Ethylsulfonyl-5-pentylsulfinyl-1,3,4-thiadiazole | 100 |
| 2-Ethylsulfonyl-5-hexylsulfinyl-1,3,4-thiadiazole | 99 |
| 2-Isopropylsulfinyl-5-sec.-butylsulfonyl-1,3,4-thiadiazole | 99 |
| 2-Butylsulfonyl-5-propylsulfinyl-1,3,4-thiadiazole | 100 |
| 2-Butylsulfonyl-5-isopropylsulfinyl-1,3,4-thiadiazole | 99 |
| 2-Butylsulfinyl-5-butylsulfonyl-1,3,4-thiadiazole | 100 |
| 2-Butylsulfonyl-5-isobutylsulfinyl-1,3,4-thiadiazole | 100 |
| 2-Butylsulfinyl-5-methylsulfonyl-1,3,4-thiadiazole | 80 |
| 2-tert.-Butylsulfinyl-5-methylsulfonyl-1,3,4-thiadiazole | 80 |
| 2-Isobutylsulfinyl-5-methylsulfonyl-1,3,4-thiadiazole | 80 |
| 2-Butylsulfonyl-5-pentylsulfinyl-1,3,4-thiadiazole | 80 |
| 2-Butylsulfonyl-5-hexylsulfinyl-1,3,4-thiadiazole | 80 |
| 2-Hexylsulfinyl-5-methylsulfonyl-1,3,4-thiadiazole | 80 |
| 2-Methylsulfonyl-5-pentylsulfinyl-1,3,4-thiadiazole | 80 |
| 2-sec.-Butylsulfinyl-5-methylsulfonyl-1,3,4-thiadiazole | 80 |
| 2-Isopentylsulfinyl-5-methylsulfonyl-1,3,4-thiadiazole | 80 |

EXAMPLE 10

Effect of prophylactic leaf treatment against grey mould (*Botrytis cinerea*) at tomato plants Young tomato plants were sprayed dripping wet with an aqueous solution of the concentratiin of active ingredient as given in the table. After drying of the sprayed on layer, the treated plats as well as untreated plants were inoculated by spraying on of a suspension of spores (about 1 million in each ml of fruit juice solution) of the grey mould pathogen *Botyris cinerea* and humidly incubated at about 20° C. in a greenhouse. After the breaking down of the untreated plants (=100% attack) the degree of attack of the treated plants was determined and the fungicidal effect calculated as follows:

$$100 - \left(100 \times \frac{\text{attack area in treated}}{\text{attack area in untreated}}\right) = \% \text{ effectiveness}$$

| Compounds according to invention | % Effectiveness after treatment with 0.025% active ingredient |
|---|---|
| 2-Ethylsulfinyl-5-ethylsulfonyl-1,3,4-thiadiazole | 100 |
| 2-Isobutylsulfinyl-5-isopropylsulfonyl-1,3,4-thiadiazole | 80 |

EXAMPLE 11

Effect of prophylactic leaf treatment against blast disease (*Piricularia oryzae*) at rice seedlings in the greenhouse Young rice plants were sprayed dripping wet with an aqueous solution having the active ingredient concentrations given in the table. After drying of the sprayed on layer the treated as well as untreated control plants were inoculated by spraying on a suspension of spores (about 200,000 per ml) of the leaf spot pathogen *Piricularia oryzae* and humidly incubated at about 25° to 27° C. in a greenhouse.

After five days it was determined what percentage of the leaf area had been attacked. From these attack area numbers the fungicidal effectiveness was calculated as follows:

$$100 - \left(100 \times \frac{\text{attack area in treated}}{\text{attack area in untreated}}\right) = \% \text{ effectiveness}$$

The compounds were formulated as 20% spray powders.

| Compounds according to invention | % Effectiveness after treatment with 0.1% active ingredient |
|---|---|
| 2-Ethylsulfinyl-5-butylsulfonyl-1,3,4-thiadiazole | 93 |
| 2-Isopropylsulfonyl-5-isopropylsulfinyl-1,3,4-thiadiazole | 90 |
| 2-Ethylsulfinyl-5-methylsulfonyl-1,3,4-thiadiazole | 90 |
| 2-Ethylsulfinyl-5-ethylsulfonyl-1,3,4-thiadiazole | 100 |
| 2-Ethylsulfinyl-5-propylsulfonyl-1,3,4-thiadiazole | 83 |
| 2-Ethylsulfinyl-5-isopropylsulfonyl-1,3,4-thiadiazole | 100 |
| 2-Ethylsulfinyl-5-sec.-butylsulfonyl-1,3,4-thiadiazole | 92 |
| 2-Isopropylsulfonyl-5-propylsulfinyl-1,3,4-thiadiazole | 96 |
| 2-Butylsulfinyl-5-isopropylsulfonyl-1,3,4-thiadiazole | 100 |
| 2-Isobutylsulfinyl-5-isopropylsulfonyl-1,3,4-thiadiazole | 98 |
| 2-Isopropylsulfonyl-5-methylsulfonyl-1,3,4-thiadiazole | 90 |
| 2-Ethylsulfonyl-5-isopropylsulfinyl-1,3,4-thiadiazole | 60 |
| 2-Methylsulfonyl-5-propylsulfinyl-1,3,4-thiadiazole | 80 |
| 2-Ethylsulfonyl-5-methylsulfinyl-1,3,4-thiadiazole | 92 |
| 2-Ethylsulfonyl-5-propylsulfinyl-1,3,4-thiadiazole | 100 |
| 2-Ethylsulfonyl-5-butylsulfinyl-1,3,4-thiadiazole | 100 |
| 2-Propylsulfinyl-5-sec.-butylsulfonyl-1,3,4-thiadiazole | 89 |
| 2-tert.-Butylsulfinyl-5-methylsulfonyl-1,3,4-thiadiazole | 90 |
| 2-Isobutylsulfinyl-5-methylsulfonyl-1,3,4-thiadiazole | 90 |

EXAMPLE 12

Seed treatment against leaf stripe (*Helminthosporium gramineum*) on barley

Barley seed with natural attack by *Helminthosporium gramineum* was untreated or teated, respectively, as indicated in the table, sowed into plastic pots filled with soil and left for germination at temperatures below +16° C. After sprouting the germs were illuminated daily with 12 hours of artificial light. After about 5 weeks all plants sprouted as well as all plants attacked by fungi were counted for each member experiment The fungicidal effect was calculated as follows:

$$100 - \left(100 \times \frac{\text{attack in treated}}{\text{attack in untreated}}\right) = \% \text{ effectiveness}$$

The compounds were employed as 20 percent formulations.

| Compounds according to invention | % Effectiveness after treatment with active ingredient g/100 kg seed | |
|---|---|---|
| | 50 g | 20 g |
| 2-Ethylsulfinyl-5-butylsulfonyl-1,3,4-thiadiazole | 99 | 98 |
| 2-Ethylsulfinyl-5-methylsulfonyl-1,3,4-thiadiazole | 100 | 100 |
| 2-Ethylsulfinyl-5-Ethylsulfonyl-1,3,4-thiadiazole | 100 | 100 |
| 2-Ethylsulfinyl-5-propylsulfonyl-1,3,4-thiadiazole | 100 | 99 |
| 2-Ethylsulfinyl-5-isopropylsulfonyl-1,3,4-thiadiazole | 100 | 99 |
| 2-Methylsulfinyl-5-propylsulfonyl-1,3,4-thiadiazole | 85 | 49 |
| 2-Ethylsulfonyl-5-(1-methylbutylsulfinyl)-1,3,4-thiadiazole | 98 | 87 |
| 2-(1-Ethylbutylsulfinyl)-5-ethylsulfonyl-1,3,4-thiadiazole | 100 | 92 |
| 2-(1-Methylbutylsulfinyl)-5-propylsulfonyl-1,3,4-thiadiazole | 92 | 89 |
| 2-(1-Ethylbutylsulfinyl)-5-propylsulfonyl-1,3,4-thiadiazole | 97 | 77 |
| 2-Butylsulfonyl-5-(1-methylbutylsulfinyl)-1,3,4-thiadiazole | 90 | 64 |
| 2-(1-Methylbutylsulfinyl)-5-(2-methylpropylsulfonyl)-1,3,4-thiadiazole | 93 | 92 |
| 2-(1-Methylbutylsulfinyl)-5-methylsulfonyl-1,3,4-thiadiazole | 99 | 100 |
| 2-(1-Ethylbutylsulfinyl)-5-methylsulfonyl-1,3,4-thiadiazole | 97 | 79 |
| 2-Ethylsulfonyl-5-isopropylsulfinyl-1,3,4-thiadiazole | 100 | — |
| 2-Methylsulfinyl-5-methylsulfonyl-1,3,4-thiadiazole | 100 | — |
| 2-Methylsulfinyl-5-propylsulfonyl-1,3,4-thiadiazole | 100 | — |
| 2-Isopropylsulfinyl-5-methylsulfonyl-1,3,4-thiadiazole | 100 | — |
| 2-Ethylsulfonyl-5-methylsulfinyl-1,3,4-thiadiazole | 100 | — |
| 2-Ethylsulfonyl-5-propylsulfinyl-1,3,4-thiadiazole | 100 | — |
| 2-Ethylsulfonyl-5-butylsulfinyl-1,3,4-thiadiazole | 100 | — |
| 2-Ethylsulfonyl-5-pentylsulfinyl-1,3,4-thiadiazole | 94 | — |
| 2-Ethylsulfonyl-5-hexylsulfinyl-1,3,4-thiadiazole | 82 | — |
| 2-Ethylsulfonyl-5-isobutylsulfinyl-1,3,4-thiadiazole | 100 | — |
| 2-Ethylsulfonyl-5-sec.-butylsulfinyl-1,3,4-thiadiazole | 100 | — |
| 2-Butylsulfonyl-5-methylsulfinyl-1,3,4-thiadiazole | 100 | — |
| 2-Propylsulfinyl-5-sec.-butylsulfonyl-1,3,4-thiadiazole | 100 | — |
| 2-Isopropylsulfinyl-5-sec.-butylsulfonyl-1,3,4-thiadiazole | 92 | — |
| 2-Ethylsulfonyl-5-tert.-butylsulfinyl-1,3,4-thiadiazole | 100 | — |
| 2-Butylsulfonyl-5-propylsulfinyl-1,3,4-thiadiazole | 100 | — |
| 2-Butylsulfonyl-5-isopropylsulfinyl-1,3,4-thiadiazole | 85 | — |
| 2-Butylsulfinyl-5-butylsulfonyl-1,3,4-thiadiazole | 69 | — |
| 2-Butylsulfonyl-5-isobutylsulfinyl-1,3,4-thiadiazole | 85 | — |
| 2-Butylsulfinyl-5-methylsulfonyl-1,3,4-thiadiazole | 69 | — |
| 2-tert.-Butylsulfinyl-5-methylsulfonyl-1,3,4-thiadiazole | 100 | — |
| 2-Isobutylsulfinyl-5-methylsulfonyl-1,3,4-thiadiazole | 69 | — |
| 2-Butylsulfonyl-5-pentylsulfinyl-1,3,4-thiadiazole | 100 | — |
| 2-Hexylsulfinyl-5-methylsulfonyl-1,3,4-thiadiazole | 100 | — |
| 2-Methylsulfonyl-5-pentylsulfinyl-1,3,4-thiadiazole | 100 | — |
| 2-sec.-butylsulfinyl-5-methylsulfonyl-1,3,4-thiadiazole | 100 | — |
| 2-Isopentylsulfinyl-5-methylsulfonyl-1,3,4-thiadiazole | 100 | — |
| Comparison compound | 5.2 g | 2.6 g |
| Methoxyethylmercurysilicate | 95 | 79 |

EXAMPLE 13

Seed treatment against stinking smut (*Tilletia caries*) in wheat

Wheat seed was contaminated with 3 g of spores of the stinking smut pathogen *Tilletia caries* for each 1 kg of wheat seed. Untreated or as in the table indicated treated grains were pressed with their bearded end into a substrate of humid loam filled in a Petri-dish and incubated for three days at temperatures below +12° C. Then the grains were removed and the Petri-dishes with the remaining stinking smut pores were further incubated at about 12° C. After about 10 days the spores were investigated for germination. The fungicidal effectiveness was calculated as follows:

$$100 - \left( 100 \times \frac{\text{germ percentage in treated}}{\text{germ percentage in untreated}} \right) = \% \text{ effectiveness}$$

The compounds were employed as 20 percent formulations.

| Name of compound | % Effectiveness with 20 g ingredient for 100 kg seed |
|---|---|
| 2-Ethylsulfinyl-5-butylsulfonyl-1,3,4-thiadiazole | 100 |
| 2-Ethylsulfinyl-5-methylsulfonyl-1,3,4-thiadiazole | 97 |
| 2-Ethylsulfinyl-5-ethylsulfonyl-1,3,4-thiadiazole | 100 |
| 2-Ethylsulfinyl-5-propylsulfonyl-1,3,4-thiadiazole | 100 |
| 2-Ethylsulfinyl-5-isopropylsulfonyl-1,3,4-thiadiazole | 100 |
| 2-Methylsulfinyl-5-propylsulfonyl-1,3,4-thiadiazole | 96 |
| 2-Butylsulfinyl-5-isopropylsulfonyl-1,3,4-thiadiazole | 100 |
| 2-Isobutylsulfinyl-5-isopropylsulfonyl-1,3,4-thiadiazole | 70 |
| 2-Hexylsulfinyl-5-isopropylsulfonyl-1,3,4-thiadiazole | 90 |
| 2-Isopropylsulfonyl-5-methylsulfinyl-1,3,4-thiadiazole | 70 |
| 2-Ethylsulfonyl-5-(1-methylbutylsulfinyl)-1,3,4-thiadiazole | 97 |
| 2-(1-Ethylbutylsulfinyl)-5-ethylsulfonyl-1,3,4-thiadiazole | 100 |
| 2-(1-Methylbutylsulfinyl)-5-propylsulfonyl-1,3,4-thiadiazole | 96 |
| 2-(1-Ethylbutylsulfinyl)-5-propylsulfonyl-1,3,4-thiadiazole | 96 |
| 2-Butylsulfonyl-5-(1-methylbutylsulfinyl)-1,3,4-thiadiazole | 99 |
| 2-(1-Methylbutylsulfinyl)-5-pentylsulfonyl-1,3,4-thiadiazole | 99 |
| 2-(1-Methylbutylsulfinyl)-5-(2-methylpropylsulfonyl)-1,3,4-thiadiazole | 100 |
| 2-Ethylsulfonyl-5-isopropylsulfonyl-1,3,4-thiadiazole | 100 |
| 2-Methylsulfinyl-5-methylsulfonyl-1,3,4-thiadiazole | 100 |
| 2-Methylsulfonyl-5-propylsulfonyl-1,3,4-thiadiazole | 100 |
| 2-Isopropylsulfinyl-5-methylsulfonyl-1,3,4-thiadiazole | 97 |
| 2-Ethylsulfonyl-5-methylsulfinyl-1,3,4-thiadiazole | 99 |
| 2-Ethylsulfonyl-5-propylsulfinyl-1,3,4-thiadiazole | 99 |
| 2-Ethylsulfonyl-5-butylsulfinyl-1,3,4-thiadiazole | 99 |
| 2-Ethylsulfonyl-5-pentylsulfinyl-1,3,4-thiadiazole | 98 |
| 2-Ethylsulfonyl-5-hexylsulfinyl-1,3,4-thiadiazole | 97 |
| 2-Ethylsulfonyl-5-isobutylsulfinyl-1,3,4-thiadiazole | 100 |
| 2-Ethylsulfonyl-5-sec.-butylsulfinyl-1,3,4-thiadiazole | 99 |
| 2-Butylsulfonyl-5-methylsulfinyl-1,3,4-thiadiazole | 100 |
| 2-Propylsulfinyl-5-sec.-butylsulfonyl-1,3,4-thiadiazole | 98 |
| 2-Ethylsulfonyl-5-tert.-butylsulfinyl-1,3,4-thiadiazole | 100 |
| 2-Butylsulfonyl-5-propylsulfinyl-1,3,4-thiadiazole | 100 |
| 2-Butylsulfonyl-5-isopropylsulfinyl-1,3,4-thiadiazole | 100 |
| 2-Butylsulfinyl-5-butylsulfonyl-1,3,4-thiadiazole | 100 |
| 2-Butylsulfonyl-5-isobutylsulfinyl-1,3,4-thiadiazole | 100 |
| 2-Butylsulfonyl-5-pentylsulfinyl-1,3,4-thiadiazole | 100 |
| 2-Butylsulfonyl-5-hexylsulfinyl-1,3,4-thiadiazole | 100 |

| Name of compound | % Effectiveness with 50 g active ingredient for 100 kg seed |
|---|---|
| 2-Butylsulfinyl-5-methylsulfonyl-1,3,4-thiadiazole | 100 |
| 2-tert.-Butylsulfinyl-5-methylsulfonyl-1,3,4-thiadiazole | 100 |
| 2-Isobutylsulfinyl-5-methylsulfonyl-1,3,4-thiadiazole | 100 |
| 2-Hexylsulfinyl-5-methylsulfonyl-1,3,4-thiadiazole | 100 |
| 2-Methylsulfonyl-5-pentylsulfinyl-1,3,4-thiadiazole | 100 |
| 2-sec.Butylsulfinyl-5-methylsulfonyl-1,3,4-thiadiazole | 100 |
| 2-Isopentylsulfinyl-5-methylsulfonyl-1,3,4-thiadiazole | 100 |
| Comparison compound | 2.6 g/100 kg |
| Methoxyethylmercurysilicate | 99 |

EXAMPLE 14

Effect of seed treatment against Septoria leaf or glume blotch (*Septoria nodorum*) on wheat Wheat seed with natural attack by *Septoria nodorum* (pathogen of speckled blotch) was sowed either untreated or treated with the compounds of the present invention indicated in the table on a humid substrate fer germination and incubated in a environmental chamber at about 6° C. After 4 weeks the part of sick germs was determined and from this the effectiveness was calculated by the following formula:

$$100 - \left( 100 \times \frac{\text{attack in treated seed}}{\text{attack in untreated seed}} \right) = \% \text{ effectiveness}$$

The compounds were employed as 20 percent formulations.

| Compound according to invention | % Effectiveness with active ingredient for 100 kg seed | | |
|---|---|---|---|
| | 50 g | 20 g | 10 g |
| 2-Ethylsulfinyl-5-butylsulfonyl-1,3,4-thiadiazole | 94 | | |
| 2-Ethylsulfinyl-5-methylsulfonyl-1,3,4-thiadiazole | 99 | 92 | 72 |
| 2-Ethylsulfinyl-5-ethylsulfonyl-1,3,4-thiadiazole | 99 | 94 | 91 |
| 2-Ethylsulfinyl-5-propylsulfonyl-1,3,4-thiadiazole | 99 | 95 | 86 |
| 2-Ethylsulfinyl-5-isopropylsulfonyl-1,3,4-thiadiazole | 99 | 91 | 72 |
| 2-Methylsulfinyl-5-propylsulfonyl-1,3,4-thiadiazole | 97 | 81 | 76 |
| Comparison material, active ingredient/100 kg seed | 5.2 | 2.6 | 1.3 g |
| Methoxyethylmercurysilicate | 99 | 96 | 84 |

EXAMPLE 15

Seed treatment against snow mould (*Fusarium nivale*) on rye

Rye seed with natural attack by *Fusarium nivale* (pathogen of the snow mould) without treatment or after treatment as indicated in the table were sowed into plant vessels filled with soil and allowed to sprout at about 6° C. After sprouting the germs were illuminated daily for 12 hours with artificial light. After about 4 weeks the degree of attack was determined in percent. The fungicidal effectiveness was calculated as follows:

$$100 - \left(100 \times \frac{\text{attack in treated}}{\text{attack in untreated}}\right) = \% \text{ effectiveness}$$

The compounds were employed as 20 percent formulations.

were sowed into each dish. After a culturing time of three weeks at 20° C. to 24° C. in the greenhouse the number of healthy peas was determined and a root evaluation was performed.

Active ingredients, amounts employed and results are presented in the following table.

Root evaluation:
4 = white roots, without fungus necrosis;
3 = white roots, slight fungus necrosis;
2 = brown roots, already considerable fungus necrosis;
1 = strong fungus necrosis, roots rotted.

| Test of limit concentration in the control of root rot (*Pythium ultimum*) | | | |
|---|---|---|---|
| | Concentration of active ingredient mg/liter soil | Number of healthy peas | Root evaluation (1–4) |
| Compound according to the invention | | | |
| 2-Ethylsulfinyl-5-methylsulfonyl-1,3,4-thiadiazole | 20 mg | 17 | 4 |
| | 40 mg | 18 | 4 |
| | 80 mg | 19 | 4 |
| 2-Ethylsulfinyl-5-ethylsulfonyl-1,3,4-thiadiazole | 20 mg | 18 | 4 |
| | 40 mg | 19 | 4 |
| | 80 mg | 19 | 4 |
| 2-Ethylsulfonyl-5-isopropylsulfinyl-1,3,4-thiadiazole | 20 mg | 17 | 4 |
| | 40 mg | 18 | 4 |
| | 80 mg | 17 | 4 |
| COMPARISON MATERIALS | | | |
| 2,5-Bis(methane-1-sulfonyl)-1,3,4-thiadiazole | 20 mg | 9 | 1 |
| | 40 mg | 8 | 1 |
| | 80 mg | 10 | 2 |
| 2-(Ethane-1-sulfonyl)-5-(methane-1-sulfonyl)-1,3,4-thiadiazole | 20 mg | 7 | 1 |
| | 40 mg | 7 | 1 |
| | 80 mg | 9 | 1 |
| Control I (3 repititions) | — | 0 | 1 |
| Contaminated soil without treatment | — | 1 | 1 |
| | — | 0 | 1 |
| Control II (3 repititions) | — | 18 | 4 |
| Steamed soil | — | 20 | 4 |
| | — | 19 | 4 |

| Compound according to invention | % effectiveness with 100 g active ingredient for 100 kg seed |
|---|---|
| 2-Ethylsulfinyl-5-butylsulfonyl-1,3,4-thiadiazole | 88 |
| 2-Ethylsulfinyl-5-methylsulfonyl-1,3,4-thiadiazole | 100 |
| 2-Ethylsulfinyl-5-ethylsulfonyl-1,3,4-thiadiazole | 100 |
| 2-Ethylsulfinyl-5-propylsulfonyl-1,3,4-thiadiazole | 100 |
| 2-Ethylsulfinyl-5-isopropylsulfonyl-1,3,4-thiadiazole | 86 |
| 2-Methylsulfinyl-5-propylsulfonyl-1,3,4-thiadiazole | 78 |

| Comparison material | active ingredient per 100 kg seed | | |
|---|---|---|---|
| | 10.4 g | 5.2 g | 2.6 g |
| Methylethylmercurysilicate | 96 | 86 | 42 |

EXAMPLE 16

Test of limit concentration in the control of root rot (*Pythium ultimum*)

20 percent active ingredient preparations in powder form were mixed uniformly with the soil strongly contaminated with *Pythium ultimum*. The treated soil was filled into clay dishes holding 0.5 liter soil and without waiting 20 grains of peas (*Pisum sativum L.* convar. medullare Alef.) of the variety "Marvel of Kelvedon"

EXAMPLE 17

Test of limit concentration in the control of Fusarium root rot (*Fusarium avenaceum*)

20 percent active ingredient containing preparations in powder form were mixed uniformly with soil strongly contaminated with Fusarium root rot (*Fusarium avenaceum*). The treated soil was filled into clay dishes holding 0.5 liter soil and without waiting 20 grains of peas (*Pisum sativum L.* convar medullare Alef.) of the variety "Marvel of Kelvedon" were sowed into each dish. After a culturing time of 18 days at 20°–24° C. in the greenhouse the number of healthy peas was determined and a root evaluation (1–4) was performed.

Active ingredients, amounts employed and results are presented in the following table.

Root evaluation:
4 = white roots, without fungus necrosis;
3 = white roots, slight fungus necrosis;
2 = brown roots, already considerable fungus necrosis;
1 = strong fungus necrosis; roots rotted.

| Test of limit concentration in the control of Fusarium root rot (*Fusarium avenaceum*) | | | |
|---|---|---|---|
| | Concentration of active ingredient mg/liter soil | Number of healthy peas | Root evaluation (1–4) |
| Compound according to invention | | | |
| 2-Ethylsulfinyl-5-propylsulfonyl-1,3,4-thiadiazole | 25 mg | 17 | 3 |
| | 50 mg | 19 | 4 |

-continued

Test of limit concentration in the control of Fusarium root rot (Fusarium avenaceum)

| | Concentration of active ingredient mg/liter soil | Number of healthy peas | Root evaluation (1-4) |
|---|---|---|---|
| | 100 mg | 20 | 4 |
| 2-Ethylsulfonyl-5-isopropylsulfinyl-1,3,4-thiadiazole | 25 mg | 14 | 4 |
| | 50 mg | 18 | 4 |
| | 100 mg | 18 | 4 |
| COMPARISON MATERIALS | | | |
| 2,5-Bis(methane-1-sulfonyl)-1,3,4-thiadiazole | 25 mg | 0 | 1 |
| | 50 mg | 0 | 1 |
| | 100 mg | 0 | 1 |
| 2-(Ethane-1-sulfonyl)-5-(methane-1-sulfonyl)-1,3,4-thiadiazole | 25 mg | 0 | 1 |
| | 50 mg | 2 | 1 |
| | 100 mg | 10 | 3 |
| Control I (3 repititions) | — | 0 | 1 |
| Contaminated soil without treatment | — | 0 | 1 |
| | — | 0 | 1 |
| Control II (3 repititions) | — | 18 | 4 |
| Steamed soil | — | 19 | 4 |
| | — | 18 | 4 |

EXAMPLE 18

Seed treatment against black loose smut (*Ustilago avenae*) on oats in the greenhouse Oat seed was immersed in an aqueous suspension of the spores of the black loose smut (*Ustilago avenae*) and subjected in a vacuum desiccator to multiple pressure changes to induce artificial contamination. After the seed had dried in air the treatments presented in the table were performed. Then for each experiment member about 300 grains were sowed into plant vessels filled with soil and the vessels were placed in a greenhouse at temperatures oscillating between 20° and 25° C. After 2½ months healthy and smutted panicles were counted and effectiveness was calculated as follows:

$$100 - \left(100 \times \frac{\text{part of smutted panicles in treated}}{\text{part of smutted panicles in untreated}}\right) = \% \text{ effectiveness}$$

| | % Effectiveness after treatment with 100 g active ingredient for 100 kg seed |
|---|---|
| Compound according to invention | |
| 2-Ethylsulfinyl-5-methylsulfonyl-1,3,4-thiadiazole | 49 |
| 2-Ethylsulfinyl-5-ethylsulfonyl-1,3,4-thiadiazole | 96 |
| Comparison material | |
| 2,5-Bis-(methane-1-sulfonyl)-1,3,4-thiadiazole | 0 |
| 2-(Ethane-1-sulfonyl)-5-(methane-1-sulfonyl)-1,3,4-thiadiazole | 0 |

What is claimed is:

1. A method of controlling fungi comprising placing into the surroundings of the fungi an effective amount of a compound of the general formula

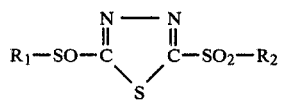

wherein $R_1$ is ethyl and $R_2$ is methyl, ethyl, propyl or isopropyl, or $R_1$ is isopropyl and $R_2$ is ethyl.

2. Method according to claim 1, wherein said compound is 2-ethylsulfinyl-5-methylsulfonyl-1,3,4-thiadiazole.

3. Method according to claim 1, wherein said compound is 2-ethylsulfinyl-5-ethylsulfonyl-1,3,4-thiadiazole.

4. Method according to claim 1, wherein said compound is 2-ethylsulfinyl-5-propylsulfonyl-1,3,4-thiadiazole.

5. Method according to claim 1, wherein said compound is 2-ethylsulfinyl-5-isopropylsulfonyl-1,3,4-thiadiazole.

6. Method according to claim 1, wherein said compound is 2-ethylsulfonyl-5-isopropylsulfinyl-1,3,4-thiadiazole.

* * * * *